(12) United States Patent
Becker et al.

(10) Patent No.: US 7,579,421 B2
(45) Date of Patent: Aug. 25, 2009

(54) POLYMERS THAT ARE SOLUBLE IN WATER OR CAN BE DISPERSED IN WATER AND CONTAIN ALKOXYLATED DIALLYLAMINE DERIVATIVES

(75) Inventors: Stefan Becker, Mannheim (DE); Lysander Chrisstoffels, Limburgerhof (DE); Ludwig Voelkel, Limburgerhof (DE); Thomas Goetz, Leimersheim (DE); Bernd Meyer-Roscher, Neustadt (DE); Wolfgang Hansch, Schwegenheim (DE); Stefanie Spilger, Schwetzingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 659 days.

(21) Appl. No.: 10/563,430

(22) PCT Filed: Jun. 19, 2004

(86) PCT No.: PCT/EP2004/006648

§ 371 (c)(1),
(2), (4) Date: Jan. 5, 2006

(87) PCT Pub. No.: WO2005/005500

PCT Pub. Date: Jan. 20, 2005

(65) Prior Publication Data

US 2006/0149013 A1    Jul. 6, 2006

(30) Foreign Application Priority Data

Jul. 7, 2003   (DE) .............................. 103 30 747

(51) Int. Cl.
*C08F 20/06* (2006.01)
(52) U.S. Cl. .................. 526/317.1; 526/310; 524/599; 524/831
(58) Field of Classification Search ................ None
See application file for complete search history.

(56) References Cited

U.S. PATENT DOCUMENTS

| | | | |
|---|---|---|---|
| 3,585,148 A | | 6/1971 | Sackis |
| 4,706,755 A | * | 11/1987 | Roark et al. ................ 166/295 |
| 5,478,883 A | * | 12/1995 | Anchor et al. .............. 524/812 |
| 5,534,183 A | * | 7/1996 | Gopalkrishnan et al. .... 510/434 |
| 5,536,440 A | * | 7/1996 | Gopalkrishnan et al. .... 510/417 |
| 5,733,861 A | * | 3/1998 | Gopalkrishnan et al. .... 510/418 |
| 5,849,853 A | | 12/1998 | Schade |
| 6,242,101 B1 | | 6/2001 | Schwalm et al. |
| 2003/0171245 A1 | * | 9/2003 | Goovaerts et al. ........... 510/444 |

FOREIGN PATENT DOCUMENTS

| | | |
|---|---|---|
| DE | 29 16 698 | 11/1979 |
| DE | 196 53 524 | 6/1998 |
| EP | 0 111 965 | 6/1984 |
| EP | 0 112 592 | 7/1984 |
| EP | 0 736 553 | 10/1996 |
| EP | 0 850 895 | 7/1998 |
| EP | 0 850 994 | 7/1998 |
| EP | 1 118 598 | 7/2001 |
| EP | 1118598 A2 * | 7/2001 |
| WO | 01/21542 | 3/2001 |

* cited by examiner

*Primary Examiner*—David Wu
*Assistant Examiner*—Vu Nguyen
(74) *Attorney, Agent, or Firm*—Oblon, Spivak, McClelland, Maier & Neustadt, P.C.

(57) ABSTRACT

Water-soluble or water-dispersible polymers comprising alkoxylated diallylamine derivatives, ethylenically unsaturated mono- or dicarboxylic acids, the anhydrides thereof or mixtures thereof and, if required, one or more further ethylenically unsaturated monomers C are prepared and are used as additives in mineral building materials, in detergents or in cosmetic formulations.

19 Claims, No Drawings

POLYMERS THAT ARE SOLUBLE IN WATER OR CAN BE DISPERSED IN WATER AND CONTAIN ALKOXYLATED DIALLYLAMINE DERIVATIVES

The present invention relates to water-soluble or water-dispersible polymers comprising alkoxylated diallylamine derivatives, ethylenically unsaturated mono- or dicarboxylic acids, the anhydrides thereof or mixtures thereof and, if required, one or more further ethylenically unsaturated monomers, processes for the preparation thereof and the use thereof as additives in mineral building materials, in detergents or in cosmetic formulations.

U.S. Pat. No. 3,585,148 describes the copolymerization of ethoxylated diallylamines and acrylamide and the use thereof as a demulsifier in dispersed oil-in-non-oily continuous phases.

The antibactericidal action of polyethoxylated diallylamines for contact lenses is claimed in DE 2916698.

The use of polyethoxylated diallylamines in detergents is claimed in EP 111 965 and EP 112 592. The synthesis of the ethoxylated diallylamines from diallylamine and the preparation of the homopolymers are likewise disclosed. Copolymers are not disclosed.

Polycarboxylates having polyether side chains or copolymers of unsaturated acids and polyether macromonomers and their use as concrete plasticizers or cement dispersants are known.

EP 736 553 describes copolymers of unsaturated dicarboxylic acids (maleic anhydride) and alkoxylated alkenyl ethers (e.g. ethoxylated allyl alcohol) which may contain up to 20 mol % of acrylic acid derivative or methacrylic acid derivative.

DE 19653524 describes water-soluble or water-dispersible polymers which contain carboxyl groups and polyalkylene oxide side chains.

EP 850 994 describes a cement additive which is prepared from an unsaturated polyalkylene glycol ether monomer and maleic anhydride.

EP 850 895 describes a cement dispersant consisting of a polycarboxylic acid having polyalkylene oxide side chains.

EP 1 118 598 likewise describes cement dispersants consisting of a polycarboxylic acid having polyalkylene oxide side chains. Ethoxylated allyl alcohol and ethoxylated methallyl alcohol are also used as monomers here.

WO 01/21542 describes a cement dispersant obtainable by polymerization of at least one compound (A) of the type $CH_2=CR_1CH_2O(R_2O)_mR_3$, where $R_1$ is hydrogen or methyl; $R_2$ is $C_2$- or $C_3$-alkylene; $R_3$ is hydrogen or methyl and m is an integer from 1 to 300, and at least one compound (B) $CH_2=CR_4COO(R_5O)_nR_6$, where $R_4$ is hydrogen or methyl, $R_5$ is $C_2$- or $C_3$-alkylene; $R_6$ is hydrogen or methyl and n is an integer from 1 to 300, and (C) at least one compound selected from the group consisting of maleic acid and maleic anhydride, and (D) at least one compound selected from the group consisting of acrylic acid, methacrylic acid and itaconic acid, and subsequent neutralization of the copolymer.

In summary, it may be said that the additives known from the prior art are still in need of improvement for the novel uses.

In particular, the plasticizing effect of the additives in mineral building materials with low water/binder ratios is as a rule still insufficient or is maintained only over a short time span. A higher dose of the plasticizer can partly compensate the deficiency but, as a rule, in addition to the uneconomical nature of such a procedure, results in much poorer achievable mechanical strength or at least unacceptable reductions in the setting rates.

It was an object of the present invention to provide additives, in particular for mineral building materials, which, with regard to their plasticizing effect, have advantages over the known additives for mineral building materials.

We have found that this object is achieved and that, surprisingly, water-soluble or water-dispersible polymers comprising (a) at least one alkoxylated diallylamine derivative (monomer A)
(b) at least one ethylenically unsaturated mono- or dicarboxylic acid, the anhydrides thereof or mixtures thereof (monomer B) and
(c) if required, one or more further ethylenically unsaturated monomers C have advantageous properties as additives or detergents, in cosmetic compositions and in particular in mineral building materials.

In spite of an excellent plasticizing effect on cement-containing building materials, the novel compounds have fewer disadvantages in setting behavior or with regard to the strength of the set building materials.

The present invention furthermore relates to the use of the polymer in detergents, in cosmetic compositions and in mineral building materials, and mineral building materials, detergents or cosmetic compositions comprising the novel polymers and processes for their preparation.

In a preferred embodiment at least one compound of the formula I

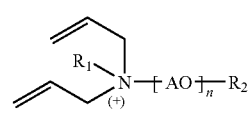

(I)

where
AO is a $C_1$-$C_{12}$-alkylene oxide, styrene oxide or a mixture of two or more types thereof, it being possible for the two or more types to be attached to one another in block form or in random form,
n is an integer from 2 to 200
$R_1$ is hydrogen, $C_1$-$C_{20}$-alkyl, $C_5$-$C_{10}$-cycloalkyl or an unsubstituted or substituted benzyl radical and
$R_2$ is hydrogen, $C_1$-$C_{30}$-alkyl, $C_5$-$C_8$-cycloalkyl, $C_6$-$C_{20}$-aryl, $C_1$-$C_{30}$-alkanoyl, $C_7$-$C_{21}$-aroyl, a sulfuric(mono) ester, a phosphoric ester, NR'R" or NR'R"R'''$^{3+}$ and
R', R" and R''', in each case independently of one another, may be identical or different and are hydrogen, a straight-chain or branched $C_1$-$C_{20}$-alkyl radical or a straight-chain or branched $C_1$-$C_{20}$-hydroxyalkyl radical, is used as monomer A.

In an embodiment which is likewise preferred, at least one compound of the formula II or the anhydrides thereof

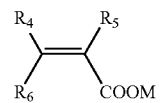

(II)

where

R$_4$ and R$_5$, independently of one another, may be either identical or different and are hydrogen or C$_1$-C$_6$-alkyl, R$_6$ is hydrogen, C$_1$-C$_6$-alkyl or a COOM group and M is hydrogen, a monovalent or divalent metal ion, ammonium or an organic ammonium ion, is used as monomer B.

Mineral building materials are to be understood as meaning formulations which contain mineral binders, such as lime, gypsum and/or in particular cement, as substantial components and sands, gravels, crushed rocks or other fillers, e.g. natural or synthetic fibers, serving as additives. The mineral building materials are converted into a ready-to-use formulation as a rule by mixing the mineral binders and the additives together with water, which formulation, if it is left to itself, becomes stone-like in the course of time in the air or under water.

It should be noted that under water applications are possible in the case of cement but not in the case of lime and give poor results in the case of gypsum.

C$_1$-C$_{12}$-alkylene oxide are understood as meaning, for example, ethylene oxide, propylene oxide, 1-butylene oxide, isomers of butylene oxide, higher alkylene oxides, such as dodecene oxide, styrene oxide and mixtures of the oxides in any desired sequence, where the ethylene oxide content should be at least 40%. Alkylene oxide is preferably ethylene oxide or mixtures of ethylene oxide and propylene oxide.

n is an integer from 2 to 200, preferably from 5 to 150, particularly preferably from 10 to 100.

A C$_1$-C$_{20}$-alkyl radical is understood as meaning a linear or branched saturated hydrocarbon chain of up to 20, preferably 1 to 10, carbon atoms, e.g. methyl, ethyl, n-propyl, isopropyl, n-butyl, tert-butyl, n-pentyl, neopentyl, n-hexyl, 2-ethylhexyl, n-octyl, 1-decyl, 1-dodecyl, etc., preferably methyl, ethyl, n-propyl or isopropyl.

A C$_5$-C$_8$-cycloalkyl radical is understood as meaning a cycloaliphatic radical of 5 to 8 carbon atoms, selected from cyclopentyl, cyclohexyl, cycloheptyl or cyclooctyl, which may be unsubstituted or substituted by 1, 2, 3 or 4 C$_1$-C$_4$-alkyl groups.

C$_6$-C$_{20}$-aryl are aryl groups which are linked via an alkylene unit and may have 6 to 20 carbon atoms, e.g. benzyl, phenyl, or ethylphenyl.

C$_1$-C$_{30}$-alkanoyl is a radical which is derived from an aliphatic carboxylic acid and, in addition to formyl, thus comprises alkyl radicals which are linked via a carbonyl group.

C$_7$-C$_{21}$-aroyl corresponds to C$_7$-C$_{21}$-arylcarbonyl and is an aryl radical which is linked via a carbonyl group and is thus derived from derivatives of benzoic acid and of naphthoic acid.

A monovalent or divalent metal ion is understood as meaning the cations of the elements of the first and second main groups of the Periodic Table of the Elements, i.e. Li$^+$, Na$^+$, K$^+$, Rb$^+$, Cs$^+$, Be$^{2+}$, Mg$^{2+}$, Ca$^{2+}$, Sr$^{2+}$ and Ba$^{2+}$ and Ag$^+$, Fe$^{2+}$, Co$^{2+}$, Ni$^{2+}$, Cu$^{2+}$, Zn$^{2+}$, Cd$^{2+}$, Sn$^{2+}$, Pb$^{2+}$ and Ce$^{2+}$. The cations of the alkali metals and alkaline earth metals Li$^+$, Na$^+$, K$^+$, Rb$^+$, Cs$^+$, Be$^{2+}$, Mg$^{2+}$, Ca$^{2+}$, Sr$^{2+}$ and Ba$^{2+}$ and Zn$^{2+}$ are preferred. Li$^+$, Na$^+$, K$^+$, Mg$^{2+}$, Ca$^{2+}$ and Zn$^{2+}$ are particularly preferred.

An organic ammonium ion is a monovalent ion which forms through protonation of a mono-, di- or trialkylamine or of a mono-, di- or trialkanolamine of 1-10 carbon atoms. Examples of mono-, di- and trialkylamines are methylamine, ethylamine, n-propylamine, isopropylamine, dimethylamine, diethylamine, di-n-propylamine, diisopropylamine, trimethylamine, and triethylamine. Examples of mono-, di- and trialkanolamines are 2-aminoethanol, diethanolamine, triethanolamine and triisopropanolamine.

R$_1$ is preferably hydrogen, methyl, ethyl, n-propyl, n-butyl or benzyl, particularly preferably hydrogen or methyl.

R$_2$ is preferably hydrogen, methyl, ethyl, n-propyl, n-butyl or phenyl, particularly preferably hydrogen or methyl.

R$_4$ and R$_5$ are preferably hydrogen or methyl

R$_6$ is preferably hydrogen, methyl or a COOM group.

M is preferably hydrogen or a monovalent metal ion.

R', R" and R'" are preferably hydrogen, methyl, ethyl or 2-hydroxyethyl.

Alkoxylated diallylamines with 2-100 mol of alkylene oxide, which preferably carry hydrogen or methyl as a further radical R$_1$, are preferably used as monomers A. Preferred alkylene oxides are ethylene oxide and propylene oxide, which may be present alone, in random sequence or in block sequence in the monomer A.

Monoethylenically unsaturated C$_3$-C$_6$-monocarboxylic acids, such as acrylic acid, methacrylic acid, crotonic acid, isocrotonic acid or 2-ethylpropenoic acid, or ethylenically unsaturated C$_4$-C$_6$-dicarboxylic acids, such as maleic acid, fumaric acid, itaconic acid or the anhydrides thereof, for example maleic anhydride, or the sodium, potassium or ammonium salts thereof are preferably used as monomers B.

In addition to the monomers A and B, the polymer may, if required, also contain monomers C. For example, C$_1$-C$_8$-alkyl esters or C$_1$-C$_4$-hydroxyalkyl esters of acrylic acid, methacrylic acid or maleic acid or esters of C$_1$C$_{18}$-alcohols with acrylic acid, methacrylic acid or maleic acid, in which C$_1$-C$_{18}$-alcohols have been alkoxylated with from 2 to 50 mol of ethylene oxide, propylene oxide, butylene oxide or mixtures thereof, e.g. hydroxyethyl acrylate, hydroxyethyl methacrylate, hydroxypropyl (meth)acrylate or butyl (meth)acrylate, can be used as monomers C.

The molar ratio of the monomers A to the monomers B is from 1:1 to 1:6, preferably from 1:2 to 2:5.

Preferred polymers contain 1-70 mol % of monomer A, 10-99 mol % of monomer B and 0-50 mol % of monomer C.

The preparation of the alkylene oxides can be effected, for example, by alkoxylation of diallylamine in a plurality of steps. In a first step, diallylamine is reacted with at least one equivalent of alkylene oxide in the presence of a solvent or in pure form. The precursor thus obtained is further reacted with alkylene oxide in the presence of a catalyst, it being possible to use all catalysts known from the prior art for the polymerization of alkylene oxides and all catalysts known from the prior art for the polymerization of alkylene oxides and compatible with amines being suitable. An overview of some catalysts is given, for example, in F. E. Bailey, Jr, J. V. Koleske, Alkylene Oxides and their Polymers, NY and Basel 1991, page 35 et seq. Basic catalysts, such as NaOH, KOH, CsOH, KOtBu, NaOMe or mixtures of the bases with crown ethers, are particularly preferably used.

The adduct of alkylene oxides and diallylamine can be further functionalized. For example, quaternization with alkylating agents is possible; the OH groups can be converted into sulfates, sulfonates, phosphates or phosphonates. Cationic, anionic or betaine structures then result.

The polymerization can be carried out by conventional polymerization methods in the form of mass polymerization, solution polymerization and, in the case of poor solubility of the monomers, also in the form of emulsions, dispersions or suspension polymerization. In the case of sufficiently poor solubility of the polymer in the reaction mixture, it is also possible to carry out the polymerization in the form of precipitation polymerization.

Said polymerization methods are preferably carried out in the absence of oxygen, preferably in a nitrogen stream. For all polymerization methods the conventional apparatuses are used, for example stirred kettles, stirred kettle cascades, autoclaves, tubular reactors and kneaders. The solution polymerization and emulsion polymerization methods are preferred. If the preparation of the novel polymers is carried out by free radical, aqueous emulsion polymerization, it is advisable to add surfactants or protective colloids to the reaction medium. The list of suitable emulsifiers and protective colloids is to be found, for example, in Houben Weyl, Methoden der organischen Chemie, Volume XIV/1 Makromolekulare Stoffe, Georg Thieme Verlag, Stuttgart 1961, page 411 et seq.

The polymerization can be carried out in solvents or diluents, e.g. toluene, o-xylene, p-xylene, cumene, chlorobenzene, ethylbenzene, industrial mixtures of alkylaromatics, cyclohexane, industrial aliphatics mixtures, acetone, cyclohexanone, tetrahydrofuran, dioxane, glycols and glycol derivatives, polyalkylene glycols and the derivatives thereof, diethyl ether, tert-butyl methyl ether, methyl acetate, isopropanol, ethanol, water or mixtures, such as isopropanol/water mixtures. A preferably used solvent or diluent is water, if required containing up to 60% by weight of alcohols or glycols. Water is particularly preferably used.

The polymerization can be carried out at from 20 to 300° C., preferably from 40 to 150° C. Depending on the choice of the polymerization conditions, it is possible to establish weight-average molecular weights ($M_w$) of, for example, from 1000 to 100,000, preferably 5000-50000. $M_w$ is determined by gel permeation chromatography.

The polymerization is preferably carried out in the presence of compounds forming free radicals. Up to 30, preferably from 0.05 to 15, particularly preferably from 0.2 to 8%, by weight, based on the monomers used in the polymerization, of these compounds are required. In the case of multicomponent initiator systems (e.g. redox initiator systems), the above weight data are based on the sum of the components.

Suitable polymerization initiators are, for example, peroxides, hydroperoxides, peroxodisulfates, percarbonates, peroxide esters, hydrogen peroxide and azo compounds. Examples of initiators, which may be water-soluble or water-insoluble, are hydrogen peroxide, dibenzoyl peroxide, dicyclohexyl peroxodicarbonate, dilauroyl peroxide, methyl ethyl ketone peroxide, di-tert-butyl hydroperoxide, acetylacetone peroxide, tert-butyl hydroperoxide, cumene hydroperoxide, tert-butyl perneodecanoate, tert-amyl perpivalate, tert-butyl perpivalate, tert-butyl perbenzoate, lithium peroxodisulfate, sodium peroxodisulfate, potassium peroxodisulfate and ammonium peroxodisulfate and azobisisobutyroritrile.

The initiators can be used alone or as a mixture with one another, for example mixtures of hydrogen peroxide and sodium peroxodisulfate. Water-soluble initiators are preferably used for the polymerization in an aqueous medium.

The known redox initiator systems may also be used as polymerization initiators. Such redox initiator systems contain at least one peroxide-containing compound in combination with a redox coinitiator, for example reducing sulfur compounds, for example bisulfites, sulfites, thiosulfates, dithionites and tetrathionates of alkali metals and ammonium compounds. Thus, combinations of peroxodisulfates with alkali metal or ammonium bisulfites may be used, for example ammonium peroxodisulfate and ammonium disulfite. The amount of the peroxide-containing compound relative to the redox coinitiator is from 30:1 to 0.05:1.

In combination with the initiators or the redox initiator systems, it is additionally possible to use transition metal catalysts, for example salts of iron, cobalt, nickel, copper, vanadium and manganese. Suitable salts are, for example, iron(II) sulfate, cobalt(II) chloride, nickel(II) sulfate or copper(I) chloride. The reducing transition metal salt is used in a concentration of from 0.1 to 1000 ppm, based on the monomers. Thus, combinations of hydrogen peroxide with iron(II) salts may be used, for example from 0.5 to 30% of hydrogen peroxide and from 0.1 to 500 ppm of Mohr's salt.

Redox coinitiators and/or transition metal catalysts, for example benzoin, dimethylaniline, ascorbic acid and complexes of heavy metals, such as copper, cobalt, iron, manganese, nickel and chromium, which are soluble in organic media, can also be used in combination with the abovementioned initiators in the polymerization in organic solvents. The amounts of redox coinitiators or transition metal catalysts usually used are from about 0.1 to 1000 ppm, based on the amount of monomers used.

In order to control the average molecular weight of polymers, it is often expedient to carry out the copolymerization in the presence of regulators. Conventional regulators, for example organic SH-containing compounds, such as 2-mercaptoethanol, 2-mercaptopropanol, 3-mercaptopropionic acid, cysteine or N-acetylcysteine, but also sodium hypophosphite or sodium bisulfite, may be used for this purpose. The polymerization regulators are generally used in amounts of from 0.1 to 10% by weight, based on the monomers. The average molecular weight can also be influenced by the choice of the suitable solvent. Thus, the polymerization in the presence of diluents having benzylic H atoms leads to reduction in the average molecular weight by chain transfer.

In order to increase the molecular weight of the polymers, it may be expedient to carry out the copolymerization in the presence of small amounts of crosslinking agents. Conventional crosslinking agents, such as bis(acrylates) of diols, such as ethylene glycol, diethylene glycol, triethylene glycol or polyethylene glycol, in an amount of 0.01-5%, based on the monomers, may be used for this purpose.

If the polymer is obtained by the method of solution polymerization in water, there is usually no need to separate off the solvent. If it is nevertheless desired to isolate the polymer, for example, spray-drying can be carried out.

If the polymer is prepared by the method of solution, precipitation or suspension polymerization in a steam-volatile solvent or solvent mixture, the solvent can be separated off by passing in steam in order to obtain an aqueous solution or dispersion. The polymer can be separated from the organic diluent also by a drying process.

The polymers are preferably present in the form of an aqueous dispersion or solution having solids contents of, preferably, from 10 to 80, in particular from 30 to 65%, by weight. The K values of the polymers are preferably in the range of 20-45.

The novel polymers are very useful as additives for cement mixtures, such as concrete or mortar. Cement is to be understood as meaning, for example, Portland cement, alumina cement or mixed cement, for example pozzolana cement, slag cement or other types. Portland cement is preferred. The copolymers are used in an amount of from 0.01 to 10, preferably from 0.05 to 3%, by weight, based on the total weight of the cement.

The polymers can be added in solid form, which is obtainable by drying, for example by spray-drying of polymer solutions or dispersions, as obtained in the polymerization, to the ready-to-use formulation of the mineral building material. It is also conceivable to formulate the copolymers with the mineral binder and to prepare the ready-to-use formulations of the mineral building material therefrom. The copolymer is preferably used in liquid, i.e. dissolved, emulsified or suspended form, for example in the form of the polymerization solution, in the formulation of the mineral building material.

For use in concrete or mortar, it may be advantageous to employ polymers which are converted into a water-soluble and hence active form, for example carboxylic acid or carboxylic anhydride structures, only in the presence of the alkaline concrete or mortar.

The slow release of the active polymer results in an activity which persists for a long time.

The novel polymers can also be used in combination with the known concrete plasticizers and/or concrete flow agents based on naphthalene/formaldehyde condensate sulfonate, melamine/formaldehyde condensate sulfonate, phenolsulfonic acid/formaldehyde condensate, lignin sulfonates and gluconates. Furthermore, they can be used together with celluloses, for example alkyl- or hydroxyalkylcelluloses, starches or starch derivatives. They can also be used in combination with high molecular weight polethylene oxides (Mw 100000-8000000).

Furthermore, additives, such as air pore formers, expansion agents, water repellents, setting retardents, setting accelerators, antifreezes, sealants, pigments, corrosion inhibitors, flow improvers, pressing-in aids, stabilizers or hollow microspheres, may be admixed. Such additives are described, for example, in EN 934.

In principle, the novel polymers can also be used together with film-forming polymers. These are to be understood as meaning those polymers whose glass transition temperature is $\leq 65°$ C., preferably $\leq 50°$ C., particularly preferably $\leq 25°$ C., very particularly preferably $\leq 0°$ C. A person skilled in the art is able to select suitable polymers on the basis of the relationship between glass transition temperature of homopolymers and the glass transition temperature of copolymers, which relationship was formulated by Fox (T. G. Fox, Bull. Am. Phys. Soc. (Ser. II) 1, 1956, 123).

Furthermore, it is often advantageous if the novel polymers are used together with antifoams. This prevents too much air in the form of air pores from being introduced into the concrete in the case of formulations of the ready-to-use mineral building materials, which air pores would reduce the strength of the set mineral building material. Suitable antifoam include in particular polyalkylene oxide-based antifoams, trialkyl phosphates, such as tributyl phosphate, and silicone-based antifoams. The ethoxylation products and the propoxylation products of alcohols of 10 to 20 carbon atoms are also suitable. The diesters of alkylene glycols or polyalkylene glycols and further conventional antifoams are also suitable. Such antifoams are usually used in amounts of from 0.05 to 10, preferably from 0.5 to 5%, by weight, based on polymers.

The antifoams can be combined with the polymer in various ways. If the polymer is present, for example, as an aqueous solution, the antifoam can be added in solid or dissolved form to the polymer solution. If the antifoam is not soluble in the aqueous polymer solution, emulsifiers or protective colloids can be used for stabilizing said antifoam.

If the novel polymer is present in the form of a solid, as obtained, for example, from spray-drying or spray-granulation in a fluidized bed, the antifoam can be admixed as a solid or can be compounded together with the polymer in the spray-drying process or spray-granulation process.

The examples which follow illustrate the invention without restricting it to said examples:

EXAMPLES

I. Analysis

Determination of the Average Molecular Weight

The determination of the weight average molecular weight was carried out by gel permeation chromatography (=GPC) using aqueous eluents.

The GPC was carried out using an apparatus combination from Agilent (Series 1100). This includes:

| | |
|---|---|
| Gasser | Model G 1322 A |
| Isocratic pump | Model G 1310 A |
| Autosampler | Model G 1313 A |
| Column oven | Model G 1316 A |
| Control module | Model G 1323 B |
| Differential refractometer | Model G 1362 A |

The eluent used in the case of polymers dissolved in water is a 0.08 mol/l TRIS buffer (pH=7.0) in distilled water+0.15 mol/l of chloride ions from NaCl and HCl.

The separation took place in a separation column combination. Columns No. 787 and 788 (8×30 mm each) from PSS with separation material GRAL BIO linear are used. The flow rate was 0.8 ml/min at a column temperature of 23° C.

The calibration is effected using polyethylene oxide standards from PPS with molecular weights of M=194–1700000 [mol/g].

Determination of the K Value

The K value of the aqueous sodium salt solutions of the copolymers were determined according to H. Fikentscher, Cellulose-Chemie, 13, 58-64 and 71-74 (1932) in aqueous solution at a pH value of 7, a temperature of 25° C. and a polymer concentration of the sodium salt of the copolymer of 1% by weight.

Determination of the Solids Content

A defined amount of sample (about 0.5-1 g) is weighed into a small aluminum dish (sample weight). The sample is dried under an IR lamp (160 volts) for 30 minutes. The mass of the sample is then determined again (final weight). The percentage solids content (SC) is calculated as follows:

$$SC = \text{final weight} \times 100 / \text{sample weight} \; [\% \text{ by weight}]$$

1. Preparation of the Reactive Alkoxylates:

Example A

Diallylamine+21 EO 2.471 kg of diallylamine and 0.126 kg of demineralized water were initially taken in a 20 l steel reactor with jacket cooling, oxide metering and internal thermometer. The reactor was briefly evacuated, and a pressure of 15.4 bar was then established at 25° C. with nitrogen. After 50 minutes, the pressure was let down to 3 bar and heating to 80° C. was effected. 1.120 kg of ethylene oxide were then metered in the course of 80 minutes so that the pressure was kept between 2.8 and 4.3 bar and the temperature did not exceed 95° C. After metering of the ethylene oxide, stirring was continued for 120 minutes and cooling to 50° C. was then effected. 1.217 kg were then discharged from the reactor. 0.1463 kg of 45% aqueous KOH solution was added to the remaining material. The temperature was increased to 103° C. and dewatering was effected at a pressure of <10 mbar. Thereafter a pressure of 2 bar was established with nitrogen and heating to 122° C. was effected and 14.817 kg of ethylene oxide were metered in in the course of 1310 minutes, the pressure being kept between 2 and 5.5 bar and the temperature not exceeding 135° C. The metering was stopped after 240 minutes, stirring was continued at 118° C., the remaining oxide was metered in the course of 110 minutes and stirring was continued for 129 minutes at this temperature. Cooling to 80° C. was effected, and 10.36 kg were discharged from the reactor. The product had an OH number of 62.9 mg KOH/g.

Example B

Diallylamine+40 EO

The product remaining in the reactor after Example 1 was heated to 86° C. in the same reactor and blanketed with nitrogen, and a pressure of 2 bar was established. Thereafter, heating to 115° C. was effected and 6.964 kg of ethylene oxide were added in the form of a gas in the course of 240 minutes so that the temperature did not exceed 130° C. and the pressure remained between 2 and 5.8 bar. After the end of the metering, stirring was continued for a further 120 minutes at 117° C. and 13.24 kg of product was discharged from the reactor. The product had an OH number of 32.03 mg KOH/g.

Example C

Diallylamine+80 EO 0.04464 kg of a 45% strength aqueous KOH solution was added to 3.574 kg of the product prepared according to Example 1, in the reactor used in Example 1, and reacted with 10.105 kg of ethylene oxide analogously to Example 2.13.51 kg of reactor discharge having an OH number of 24.13 mg KOH/g were obtained.

Quaternization

Example 1

Diallylamine+20 EO Quaternized 548.18 g of diallylamine+20 EO were melted at 60° C. in 1 l glass reactor with water bath heating, anchor stirrer, internal thermometer, reflux condenser and dropping funnel. 67.10 g of dimethyl sulfate were uniformly added dropwise to this melt in the course of one hour. After the end of the addition, stirring was continued for a further 2.5 hours at 60° C. in order to complete the reaction.

Example 2

Diallylamine+40 EO Quaternized 260.00 g of diallylamine+40 EO were melted at 65° C. in a 500 ml four-necked flask with water bath heating, anchor stirrer, internal thermometer, reflux condenser and dropping funnel. 16.74 g of dimethyl sulfate were uniformly added dropwise to this melt in the course of one hour. After the end of the addition, stirring was continued for a further 2 hours at 65° C. in order to complete the reaction.

II. Methods for the Preparation of the Copolymers

Example 1

306.21 g of water are initially taken in a 1 l glass reactor with anchor stirrer, thermometer, nitrogen inlet or reflux condenser and dropping funnel and are heated to 100° C. For blanketing, nitrogen is passed into the reactor. 192 g of diallylamine +20 EO, dissolved in 48 g of water, and 56.57 g of acrylic acid are added dropwise under reflux in the course of 5 hours, and 18.65 g of a 20% strength sodium peroxodisulfate solution and 18.65 g of a 20% strength sodium hypophosphite solution in the course of 5.25 hours. In order to complete the copolymerization, polymerization is continued for a further 1 hour, cooling is then carried out and neutralization is effected with 50% strength sodium hydroxide solution.

Example 2

200 g of diallylamine+20 EO, dissolved in 294.91 g of water, are initially taken in a 1 l glass reactor with anchor stirrer, thermometer, nitrogen inlet, reflux condenser and dropping funnel and are heated to 100° C. For blanketing, nitrogen is passed into the reactor. 58.93 g of acrylic acid are added dropwise under reflux in the course of 5 hours, and 19.4 g of a 20% strength sodium peroxodisulfate solution and 19.4 g of a 20% sodium hypophosphite solution in the course of 5.25 hours. In order to complete the copolymerization, polymerization is continued for a further 1 hour, cooling is then carried out and neutralization is effected with 50% strength sodium hydroxide solution.

Example 3

347.45 g of water are initially taken in a 1 l glass reactor with anchor stirrer, thermometer, nitrogen inlet, reflux condenser and dropping funnel and are heated to 100° C. For blanketing, nitrogen is passed into the reactor. 198.14 g of diallylamine +20 EO, quaternized with 24.24 g of dimethyl sulfate and dissolved in 55.6 g of water, and 58 g of acrylic acid are added dropwise under reflux in the course of 5 hours, and 21.05 g of a 20% strength sodium peroxodisulfate solution and 14 g of a 20% sodium hypophosphite solution in the course of 5.25 hours. In order to complete the copolymerization, polymerization is continued for a further 1 hour, cooling is then carried out and neutralization is effected with 50% strength sodium hydroxide solution.

Example 4

325.63 g of water are initially taken in a 1 l glass reactor with anchor stirrer, thermometer, nitrogen inlet, reflux condenser and dropping funnel and are heated to 100° C. For blanketing, nitrogen is passed into the reactor. 290.22 g of diallylamine+40 EO, dissolved in 156.28 g of water, and 45 g of acrylic acid are added dropwise under reflux in the course of 5 hours, and 25.13 g of a 20% strength sodium peroxodisulfate solution and 16.72 g of a 20% strength sodium hypophosphite solution in the course of 5.25 hours. In order to complete the copolymerization, polymerization is continued for a further 1 hour, cooling is then carried out and neutralization is effected with 50% strength sodium hydroxide solution.

Example 5

346.45 g of water are initially taken in a 1 l glass reactor with anchor stirrer, thermometer, nitrogen inlet, reflux condenser and dropping funnel and are heated to 100° C. For blanketing, nitrogen is passed into the reactor. 233.15 g of diallylamine+40 EO, quaternized with 15.01 g of dimethyl sulfate and dissolved in 62.04 g of water, and 36 g of acrylic acid are added dropwise under reflux in the course of 5 hours, and 21.3 g of a 20% strength sodium peroxodisulfate solution and 14.2 g of a 20% strength sodium hypophosphite solution in the course of 5.25 hours. In order to complete the copolymerization, polymerization is continued for a further 1 hour, cooling is then carried out and neutralization is effected with 50% strength sodium hydroxide solution.

Example 6

281.42 g of water are initially taken in a 1 l glass reactor with anchor stirrer, thermometer, nitrogen inlet, reflux condenser and dropping funnel and are heated to 100° C. For blanketing, nitrogen is passed into reactor. 250.32 g of diallylamine+40 EO, dissolved in 134.49 g of water, and 38.78 g of acrylic acid are added dropwise under reflux together with 0.217 g of hydroquinone monomethyl ether in the course of 5 hours, and 21.71 g of a 20% strength sodium peroxodisulfate solution and 14.43 g of a 20% strength sodium hypophosphite solution in the course of 5.25 hours. In order to complete the copolymerization, polymerization is continued for a further 1 hour, cooling is then carried out and neutralization to pH 6.5-7.0 is effected with 50% strength sodium hydroxide solution.

Example 7

317.43 g of water and 96.00 g of diallylamine+20 EO are initially taken in a 1 l glass reactor with anchor stirrer, thermometer, nitrogen inlet, reflux condenser and dropping funnel and are heated to 100° C. For blanketing, nitrogen is passed into the reactor. 96.00 g of diallylamine+20 EO, dissolved in 51.69 g of water are added dropwise under reflux, together with 3.73 g of sodium hypophosphite and 56.57 g of acrylic acid, in the course of 10 hours, and 18.65 g of a 20% strength sodium peroxodisulfate solution in the course of 10.25 hours. In order to complete the copolymerization, polymerization is continued for a further 1 hour, cooling is then carried out and neutralization to pH 6.5-7.0 is effected with 50% strength sodium hydroxide solution.

Example 8

209.23 g of water and 61.98 g of diallylamine+40 EO are initially taken in a 1 l glass reactor with anchor stirrer, thermometer, nitrogen inlet, reflux condenser and dropping funnel and are heated to 100° C. For blanketing, nitrogen is passed into the reactor. 61.98 g of diallylamine+40 EO, dissolved in 33.37 g of water are added dropwise under reflux, together with 2.15 g of sodium hypophosphite and 19.21 g of acrylic acid, in the course of 10 hours, and 10.75 g of a 20% strength sodium peroxodisulfate solution in the course of 10.25 hours. In order to complete the copolymerization, polymerization is continued for a further 1 hour, cooling is then carried out and neutralization to pH 6.5-7.0 is effected with 50% strength sodium hydroxide solution.

Example 9

26.70 g of water are initially taken in a 1 l glass reactor with anchor stirrer, thermometer, nitrogen inlet, reflux condenser and dropping funnel and are heated to 100° C. For blanketing, nitrogen is passed into the reactor. 154.40 g of diallylamine +20 EO dissolved in 83.14 g of water, and 45.59 g of acrylic acid are added dropwise under reflux in the course of 5 hours, and 3.0 g of VA 086 azo initiator, dissolved in 127.0 g of water, and 15.0 g of a 20% strength sodium hypophosphite solution in the course of 5.25 hours. In order to complete the copolymerization, polymerization is continued for a further 1 hour, cooling is then carried out and neutralization to pH 6.5-7.0 is effected with 50% strength sodium hydroxide solution.

Example 10

187.18 g of water and 58.10 g of diallylamine+40 EO are initially taken in a 1 l glass reactor with anchor stirrer, thermometer, nitrogen inlet, reflux condenser and dropping funnel and are heated to 70° C. For blanketing, nitrogen is passed into the reactor. When the temperature has been reached, 58.10 g of diallylamine+40 EO, dissolved in 31.28 g of water, are added dropwise together with 0.64 g of sodium hypophosphite and 11.26 g of acrylic acid, in the course of 10 hours, and 12.73 g of a 15% strength sodium peroxodisulfate solution in the course of 10.25 hours. In order to complete the copolymerization, polymerization is continued for a further 1 hour, cooling is then carried out and neutralization to pH 6.5-7.0 is effected in 50% strength sodium hydroxide solution.

Example 11

210.00 g of water and 89.86 g of diallylamine+40 EO are initially taken in a 1 l glass reactor with anchor stirrer, thermometer, nitrogen inlet, reflux condenser and dropping funnel and are heated to 70° C. For blanketing, nitrogen is passed into the reactor. When the temperature has been reached, 17.41 g of acrylic acid, 201.5 g of 50% strength aqueous solution of polyethylene glycol methyl ether methacrylate (from Aldrich, Mn about 2080) and 1.04 g of sodium hypophosphite are added dropwise in the course of 9 hours, and 13.50 g of a 23.1% strength sodium peroxodisulfate solution in the course of 9.25 hours. In order to complete the copolymerization, polymerization is continued for a further 1 hour, cooling is then carried out and neutralization to pH 6.5-7.0 is effected with 50% strength sodium hydroxide solution.

Test methods for concrete plasticizers based on EN 196 or DIN 18555 Part 2:

Apparatus:
Mixer type 203 (from Testing Bluhm und Feuerhard GmbH)
Stopwatch
Laboratory balance (accuracy +−1 g)
Flow table d=300 mm (from Testing Bluhm und Feuerhard GmbH)
Conical mold
Dropping funnel with tube connection
Spoon
Air pore content meter (from Testing Bluhm und Feuerhard GmbH)
Vibrating table type 2.0233 (from Testing Bluhm und Feuerhard GmbH)
Prism mold (L×B×H=16 cm×4 cm×4 cm)
Starting materials: cement:additive 1:3; sieve line 0/2
1500 g of standard sand CEN I-III
500 g of Heidelberg cement CEM I 32,5 R
225 g of water (if required, including plasticizer)
⇒water/cement 0.45

Plasticizer: 0.1-0.3% of a suitable antifoam is added to the plasticizer about 1 day before test.

Note: The plasticizer addition is calculated as solid substance, based on the proportion of cement. The amount of water added by the plasticizer is taken into account when calculating the total amount of water for establishing the water/cement value.

Carrying Out the Test a) Preparation of the Mortar

The total amount of the dry mix (cement+sand) is homogeneously mixed for 1 minute using the mixer type 203.

The wet component is then metered in continuously for a period of 30 seconds by means of a dropping funnel.

After stirring for a further 3 minutes, the preparation of mortar is complete. The first measurement of the flowability is then carried out.

Water or Water/Plasticizer Mixture b) Flow Test According to DIN 18555 Part 2

For determining the flowability, the conical mold should be placed in the center of the glass plate of the flow table, the mortar should be introduced in two layers and each layer should be compacted by pressing with the spoon. During filling, the conical mold should be pressed onto the glass plate with a hand.

The projecting mortar should be scrapped off and the free surface of the flow table should be cleaned. Thereafter, the conical mold should slowly be drawn perpendicularly upward and the mortar should be spread on the glass table with 15 strokes.

The diameter of the spread mortar should then be measured in two directions at right angles to one another. The result should be stated as the arithmetic mean in cm, accurately to 0.5 cm.

The determination is carried out after 5, 30, 60, and 90 minutes. Before each measurement, the mortar is briefly stirred up.

c) Air Content of the Mortar Based on DIN 18555 Part 2

The air content of the fresh mortar is measured using an adjusted tester of 1 dm$^3$ capacity according to the pressure equilibration method.

For this purpose mortar is introduced into the 1 l container of the air pore content meter, while the mortar is compacted for 60 seconds on the vibrating table.

The upper part of the tester is then placed on the cleaned ground edge of the container and the apparatus is closed.

The still free volume of the apparatus is filled with water. A defined pressure is generated in the chamber. After pressure equilibration has been achieved, the air pore content is read directly on the scale mounted on the upper part.

The air pore content expressed as amount by volume in %, is stated with an accuracy of measurement of 0.1%.

and optionally, monomer C; wherein the mole ratio of monomer A to monomer B is 1:1 to 1:6; and (a) monomer A is at least one alkoxylated diallylamine, (b) monomer B is at least one ethylenically unsaturated mono- or dicarboxylic acid, anhydride thereof, or mixtures thereof, and (c) monomer C is one or more additional ethylenically unsaturated monomers.

2. The polymer of claim 1, wherein monomer A is least one compound of the formula I

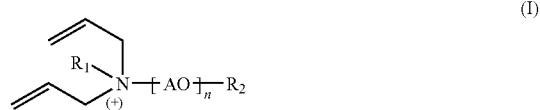

where

AO is a $C_1$-$C_{12}$-alkylene oxide, styrene oxide or a mixture of two or more types thereof, it being possible for the two or more types to be attached to one another in block form or in random form, n is an integer from 2 to 200

$R_1$ is hydrogen, $C_1$-$C_{20}$-alkyl, $C_5$-$C_{10}$-cycloalkyl or an unsubstituted or substituted benzyl radical and $R_2$ is hydrogen, $C_1$-$C_{30}$-alkyl, $C_5$-$C_8$-cycloalkyl, $C_6$-$C_{20}$-aryl, $C_1$-$C_{30}$-alkanoyl, $C_7$-$C_{21}$-aroyl, a sulfuric(mono) ester, a phosphoric ester, NR'R'' or NR'R''R'''$^{3+}$ and R', R'' and R''', in each case independently of one another, may be identical or different and are hydrogen, a straight-chain or branched $C_1$-$C_{20}$-alkyl radical or a straight-chain or branched $C_1$-$C_{20}$-hydroxyalkyl radical.

3. The polymer of claim 1, wherein monomer B is at least one compound of the formula II or the anhydrides thereof

|  | Solid [%] | pH value | K value [1% in H$_2$O] | Mn Number average | Mw Weight average | Plasticizer Dose | Flowability | | | |
|---|---|---|---|---|---|---|---|---|---|---|
|  |  |  |  |  |  |  | 5 min. | 30 min. | 60 min. | 90 min. |
| Ex. 1. | 38.8 | 6.9 | 24.9 | 5400 | 19700 | 0.20% | 17.5 | 16.4 | 15.3 | 14.3 |
| Ex. 2. | 44.2 | 6.9 | 26.8 | 5900 | 24500 | 0.20% | 17.1 | 15.9 | 15.8 | 14.4 |
| Ex. 3. | 38.6 | 6.7 | 22.9 | 6000 | 35900 | 0.30% | 17.0 | 15.3 | 14.5 | 14.6 |
| Ex. 4. | 39.4 | 6.8 | 29.5 | 5200 | 19600 | 0.30% | 18.1 | 18.1 | 17.2 | 16.7 |
| Ex. 5. | 41.7 | 7.0 | 24.2 | 4100 | 12200 | 0.30% | 16.1 | 15.2 | 13.5 | 13.7 |
| Ex. 6. | 39.5 | 6.9 | 27.8 | 8200 | 30100 | 0.30% | 18.5 | 17.9 | 17.2 | 16.2 |
| Ex. 7. | 38.5 | 6.8 | 26.7 | 5900 | 19600 | 0.20% | 16.7 | 15.6 | 13.8 | — |
| Ex. 8. | 36.2 | 7.0 | 27.3 | 5300 | 15000 | 0.20% | 16.6 | 15.8 | 13.4 | — |
| Ex. 9. | 38.2 | 6.7 | 30.2 | 6800 | 21500 | 0.20% | 15.6 | 14.9 | 13.5 | — |
| Ex. 10. | 35.5 | 6.9 | 32.6 | 6400 | 33000 | 0.20% | 18.1 | 16.8 | 15.4 | 14.7 |
| Ex. 11 | 39.0 | 6.7 | 42.1 | 9100 | 84000 | 0.20% | 15.6 | 15.6 | 14.3 | 13.0 |

We claim:

1. A water-soluble or water-dispersible polymer, wherein the polymer is obtained by free radical polymerization of a monomer composition comprising monomer A, monomer B, where $R_4$ and $R_5$, independently of one another, may be either identical or different and are hydrogen or $C_1$-$C_6$-alkyl, $R_6$ is hydrogen, $C_1$-$C_6$-alkyl or a COOM group and M is hydrogen, a monovalent or divalent metal ion, ammonium or an organic ammonium ion.

4. The polymer of claim 1 wherein the molar ratio of monomer A to monomers B is from 1:1 to 2:5.

5. The polymer of claim 1, wherein the weight average molecular weight $M_w$ of the polymer is from 1000 to 100,000.

6. The polymer of claim 1 which has a K value of from 20 to 50.

7. A mineral building material comprising cement, water, at least one polymer of claim 1, and at least one additive.

8. The polymer of claim 2, wherein the molar ratio of monomer A to monomer B is from 1:2 to 2:5.

9. The polymer of claim 3, wherein the molar ratio of monomer A to monomer B is from 1:2 to 2:5.

10. The polymer of claim 2, wherein the molar ratio of monomer A to monomer B is from 1:2 to 1:5.

11. The polymer of claim 3, wherein the molar ratio of monomer A to monomer B is from 1:2 to 1:5.

12. The polymer of claim 3, wherein the weight average molecular weight $M_w$ of the polymer is from 1000 to 1000,000.

13. The polymer of claim 3, wherein the weight average molecular weight $M_w$ of the polymer is from 1000 to 100,000.

14. The polymer of claim 4, wherein the weight average molecular weight $M_w$ of the polymer is from 1000 to 100,000.

15. The polymer of claim 2, which has a K value of from 20 to 50.

16. The polymer of claim 3, which has a K value of from 20 to 50.

17. The polymer of claim 1, wherein the mole ratio of monomer A to monomer B is 1:2 to 2:5; monomer A is at least one alkoxylated diallylamine; monomer B is at least one ethylenically unsaturated mono- or dicarboxylic acid, anhydride thereof, or mixtures thereof; and monomer C is excluded from the monomer composition.

18. A mineral building material comprising cement, water, and at least one polymer of claim 4.

19. A mineral building material comprising cement, water, and at least one polymer polymer of claim 8.

* * * * *